US011064878B2

(12) United States Patent
Takeno

(10) Patent No.: US 11,064,878 B2
(45) Date of Patent: Jul. 20, 2021

(54) OCT APPARATUS

(71) Applicant: NIDEK CO., LTD., Aichi (JP)

(72) Inventor: Naoki Takeno, Aichi (JP)

(73) Assignee: NIDEK CO., LTD., Aichi (JP)

(*) Notice: Subject to any disclaimer, the term of this patent is extended or adjusted under 35 U.S.C. 154(b) by 0 days.

(21) Appl. No.: 16/427,773

(22) Filed: May 31, 2019

(65) Prior Publication Data
US 2019/0365219 A1 Dec. 5, 2019

(30) Foreign Application Priority Data
Jun. 4, 2018 (JP) .............................. JP2018-107312

(51) Int. Cl.
*A61B 3/10* (2006.01)
*A61B 5/00* (2006.01)
(Continued)

(52) U.S. Cl.
CPC ............ *A61B 3/102* (2013.01); *A61B 3/0025* (2013.01); *A61B 3/12* (2013.01); *A61B 5/004* (2013.01); *A61B 5/0066* (2013.01)

(58) Field of Classification Search
CPC ..... A61B 3/102; A61B 3/1241; A61B 3/0025; A61B 3/1233; A61B 3/0058; A61B 3/12; A61B 3/0091; A61B 5/004; A61B 5/0066; A61B 8/00; A61B 2034/105; A61B 2034/107; A61B 2034/2051; A61B 2034/2055; A61B 2090/3735; A61B 2090/378; A61B 34/10; A61B 34/20; A61B 5/0042; A61B 5/055; A61B 6/032; A61B 6/037; A61B 6/501; A61B 8/0808; A61B 3/0033; A61B 3/1005; A61B 3/113; A61B 3/145; A61B 5/0059; A61B 5/02; A61B 5/0261; A61B 5/7275; A61B 3/1225; A61B 3/152; A61B 8/4416; A61B 8/485; G06T 7/0012; G06T 11/20; G06T 17/00; G06T 19/003; G06T 19/20; G06T 1/60; G06T 2200/04; G06T 2200/24; G06T 2207/10088; G06T 2207/20101; G06T 2207/30016; G06T 2207/30241; G06T 2210/41; G06T 2219/028; G06T 2207/10101; G06T 2207/30041;
(Continued)

(56) References Cited
U.S. PATENT DOCUMENTS
2017/0112377 A1* 4/2017 Shiba ........................ G06T 7/11

FOREIGN PATENT DOCUMENTS
JP 2018-19771 A 2/2018

* cited by examiner

*Primary Examiner* — Brandi N Thomas
(74) *Attorney, Agent, or Firm* — Sughrue Mion, PLLC

(57) ABSTRACT

An OCT apparatus includes an OCT optical system that acquires an OCT signal based on measurement light applied to a subject and reference light, and a processor. The processor controls the OCT optical system based on a predetermined trigger to execute an imaging sequence in which a plurality of temporally different OCT signals are acquired in each of a first region on a subject and a second region adjacent to or partially overlapping with the first region, and imaging conditions are different from each other between the first region and the second region. The processor obtain OCT motion contrast data of the subject based on the plurality of OCT signals acquired through the imaging sequence in the first region and the second region.

14 Claims, 10 Drawing Sheets

(51) Int. Cl.
*A61B 3/12* (2006.01)
*A61B 3/00* (2006.01)

(58) Field of Classification Search
CPC . G06T 2207/20221; G06T 2207/30104; G06T 5/50; G06T 7/0016; G06T 7/11; G06F 3/04815; G06F 3/04842; G06F 3/04847
USPC ......... 351/200, 205–206, 209–211, 221–233
See application file for complete search history.

US 11,064,878 B2

OCT APPARATUS

CROSS-REFERENCE TO RELATED APPLICATION

This application claims priority from Japanese Patent Application No. 2018-107312 filed on Jun. 4, 2018, the entire subject-matter of which is incorporated herein by reference.

TECHNICAL FIELD

The present disclosure relates to an OCT apparatus which acquires OCT motion contrast data of a subject.

BACKGROUND

In recent years, an apparatus which obtains motion contrast by using an OCT technique has been proposed (for example, refer to JP-A-2018-19771). JP-A-2018-19771 discloses that an OCT signal is acquired in a first imaging range which is an imaging range of OCT motion contrast data of a subject, and acquires an OCT signal in higher density in a second imaging range which is set in a part of the first imaging range.

An imaging time is necessary in acquisition of OCT motion contrast data more than in acquisition of typical OCT data, and this may be a burden on an examiner and an examinee.

In a case of the method disclosed in JP-A-2018-19771, the second imaging range totally overlaps with the first imaging range, and thus OCT motion contrast data in the second imaging range is doubly imaged.

SUMMARY

An object of the disclosure is to provide an OCT apparatus capable of favorably obtaining motion contrast data.

According to a first aspect of the present disclosure, there is provided an OCT apparatus including:

an OCT optical system configured to acquire an OCT signal based on measurement light applied to a subject and reference light; and a processor, in which the processor is configured to:

control the OCT optical system based on a predetermined trigger to execute an imaging sequence in which a plurality of temporally different OCT signals are acquired in each of a first region on a subject and a second region adjacent to or partially overlapping with the first region, and imaging conditions are different from each other between the first region and the second region, and obtain OCT motion contrast data of the subject based on the plurality of OCT signals acquired through the imaging sequence in the first region and the second region.

According to the present disclosure, it is possible to favorably obtain motion contrast data.

DETAILED DESCRIPTION

However, a description will be made of typical embodiments in the present disclosure.

Figure 1:
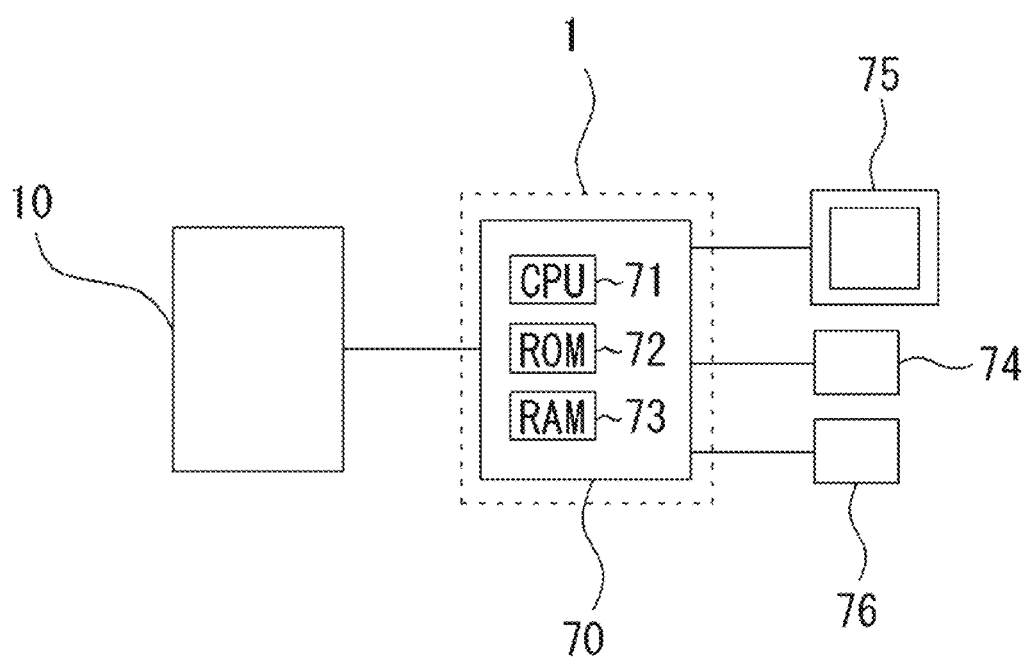
FIG. 1 is a block diagram schematically illustrating one Example.

An optical coherence tomography apparatus (OCT apparatus) according to the present embodiment may include, for example, an OCT optical system and a control unit (processor) (refer to FIG. 1). Here, the control unit may be provided to control the OCT optical system. For example, the control unit may be used to control the overall OCT apparatus including the OCT optical system.

<Fundamental Configuration>

The OCT optical system (refer to FIG. 2) may be used to acquire, for example, an OCT signal based on measurement light applied to a subject and reference light. The OCT optical system may be mainly provided with, for example, an OCT light source, a light splitter, a measurement optical system, a reference optical system, and an optical detector. In this case, the light splitter may be provided to split light from the OCT light source into measurement light and reference light. The measurement light may be guided to a subject via the measurement optical system. Interference light generated through interference between measurement light reflected at the subject and the reference light may be received by the detector.

The measurement optical system may include, for example, a scanning unit (for example, an optical scanner). The scanning unit may be provided to apply measurement light in XY directions (transverse directions) on a subject. For example, the control unit may control the scanning unit to apply measurement light to a set scanning position.

The reference optical system may be provided to generate, for example, reference light. The reference light may be combined with reflected light acquired through reflection of measurement light at a subject. The reference optical system may be a Michelson type optical system, and may be a Mach-Zehnder type optical system.

The optical detector may be provided to detect an interference state between measurement light and reference light. In a case of a Fourier domain OCT, for example, a spectral intensity of interference light may be detected by the optical detector, and an OCT signal may be acquired through Fourier transform on the spectral intensity data.

The control unit may acquire, for example, an OCT signal (also referred to as OCT data) of a subject on the basis of a light reception signal detected by the OCT optical system. The control unit may acquire a B-scan OCT signal by arranging OCT signals obtained at different positions through, for example, scanning with measurement light. A three-dimensional OCT signal may be acquired by arranging OCT signals in a two-dimensional range regarding a direction orthogonal to a depth direction. The control unit may store the obtained OCT signal in a storage unit. The control unit may display an obtained result on a display unit.

<Acquisition of Motion Contrast Data>

Figure 3A:
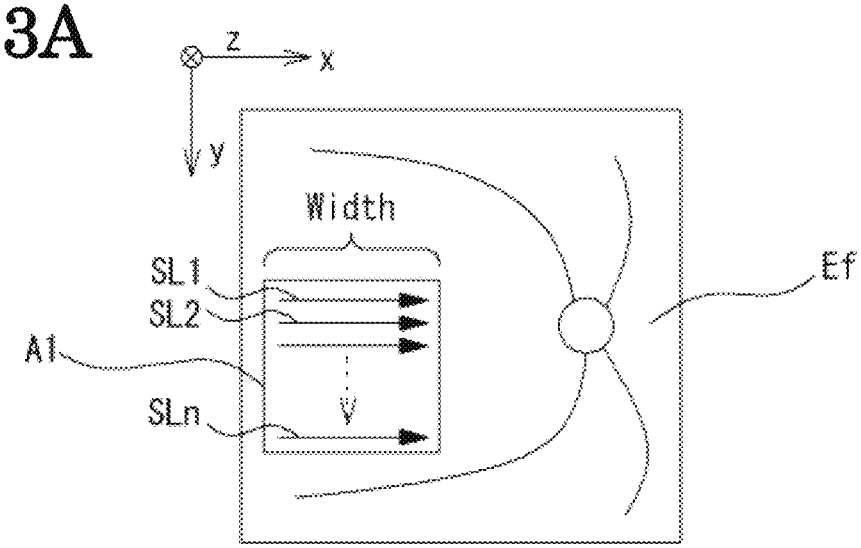
FIGS. 3A to 3C are diagrams for explaining acquisition of motion contrast.

The control unit may process, for example, an OCT signal (OCT data) of a subject so as to acquire OCT motion contrast data (hereinafter, referred to as MC data) (for example, refer to FIGS. 3A to 3C). In this case, the control unit may process, for example, two OCT signals which are temporally different from each other at an identical position, so as to acquire MC data. Here, the MC data may be data in which, for example, movement of a blood flow of a subject is generated as an image. In this case, the MC data may be data in which movement of a blood flow is expressed as a luminance value.

The control unit may be acquire B-scan MC data by arranging, for example, pieces of MC data at different positions. The control unit may acquire three-dimensional MC data may be acquired by arranging pieces of MC data in a two-dimensional range regarding a direction orthogonal to a depth direction. The control unit may process the three-dimensional MC data so as to acquire front MC data.

As a method of calculating OCT data in order to acquire MC data, for example, there may be a method of calculating an intensity difference or an amplitude difference of complex OCT data, a method (Speckle variance) of calculating a variance or a standard deviation of intensities or amplitudes of complex OCT data, a method of calculating a phase difference or a variance of complex OCT data, a method of calculating a vector difference of complex OCT data, and a method of multiplying a phase difference of a complex OCT signal by a vector difference thereof. Refer to, for example, JP-A-2015-131107 with respect to one of calculation methods.

In a case where an OCT signal which is a basis of MC data is obtained, the control unit may control, for example, the scanning unit to scan an identical scanning line with measurement light a plurality of times, and may thus obtain a plurality of temporally different B-scan OCT signals. The control unit may obtain B-scan MC data by processing the plurality of temporally different B-scan OCT signals.

The control unit may scan each of a plurality of scanning lines forming a two-dimensional scanning range with measurement light a plurality of times. The control unit may acquire B-scan MC data by processing a plurality of temporally different B-scan OCT signals with respect to each scanning line. The control unit may acquire three-dimensional MC data on the basis of B-scan MC data in each scanning line.

<MC Data Imaging Sequence>

The control unit may execute the following imaging sequence by controlling the OCT optical system on the basis of a predetermined trigger. An imaging range of MC data in the imaging sequence may be roughly divided into, for example, a first region and a second region. In this case, the first region and the second region may be adjacent to each other or may partially overlap each other. Each region may be set in advance, and may be automatically or manually set on the basis of an image of another subject (details thereof will be described later). Preferably, the second region is a part of interest such as a disease part, and the first region is a peripheral part thereof. A case where the first region and the second region are "adjacent" to each other is not limited to a case where a gap between the regions is zero, and may be a case where an allowable extent of a gap may be generated therebetween.

In the imaging sequence of the present embodiment, operations of acquiring OCT signals (OCT data) for the first region and the second region on a subject may be consecutively performed on the basis of a single trigger signal. In this case, in order to obtain MC data for each of the first region and the second region, a plurality of temporally different pieces of OCT data for each of the first region and the second region are acquired.

In this case, in the imaging sequence of the present embodiment, imaging conditions are different from each other between the first region and the second region. As a result, in the present embodiment, MC data having a higher S/N ratio in the second region than in the first region may be acquired.

For example, the control unit may execute an imaging sequence in which times required to acquire a plurality of OCT signals which are bases of MC data are different from each other per unit area.

For example, in the imaging sequence, the number of A-scans per unit area in the second region may be set to be larger than in the first region. In this case, the time required to acquire a plurality of OCT signals which are bases of MC data in the second region is longer than in the first region. As a result of the imaging sequence, an S/N ratio of MC data in the second region tends to be higher than in the first region.

As a specific example of one of imaging sequences in which the number of A-scans per unit area in the second region is set to be larger than in the first region, OCT data acquisition densities may be different from each other between the first region and the second region. In other words, the OCT data may be acquired in higher density in the second region than in the first region. In this case, the number of scanning points per scanning amount may be set to be larger in the second region than in the first region. The number of times of repeatedly acquiring OCT data at an identical position may be set to be larger in the second region than in the first region.

As a result of the imaging sequence, MC data having relatively low image quality is obtained in the first region, and MC data with high image quality based on high-density OCT data is obtained in the second region. The MC data in the second region is more advantage in checking either one of an abnormal part of a blood vessel or the like, and a blood vessel state at a feature part. Since the first region does not completely overlap with the second region, an imaging time for MC data in the entire imaging range can be reduced. In other words, in the imaging sequence of the present embodiment, it is possible to obtain MC data having a necessary information amount for each region while reducing an imaging time.

The control unit may control, for example, the OCT optical system to obtain MC data in an imaging range set by a setting unit as moving images. The control unit may display the moving images of the MC data on the display unit. Consequently, the MC data can be checked as the moving images, and thus a change in a blood flow can be checked. Of course, there is no limitation to moving images, and the control unit may obtain still images of MC data in a set imaging range.

The control unit may analyze the acquired MC data in the imaging range so as to obtain an analysis parameter. Consequently, for example, an analysis parameter based on MC data of a part of interest can be obtained, and thus the part of interest can be appropriately diagnosed. In this case, when image data acquired in advance is MC data, an analysis process may be performed on both of the MC data acquired in advance and MC data in an imaging range, and an analysis parameter based on each piece of the data may be displayed on the display unit. In a case where MC data in an imaging range is obtained as moving images, the control unit may control the OCT optical system to repeatedly acquire MC data, and may display the acquired MC data as live images on the display unit.

For example, in a case where second MC data is obtained as front moving images or three-dimensional moving images, the OCT optical system may be controlled such that MC data at each position may be measured by taking into consideration a blood flow rate in a subject. In this case, a time interval at which measurement light is applied again at an identical position may be set such that changes in a plurality of temporally different OCT signals at the identical position due to a blood flow change can be detected.

<Change of OCT Data Acquisition Density Based on Adjustment of Scanning Amount>

The control unit may control the scanning unit to make scanning amounts per unit time different from each other between the first region and the second region, so that densities of acquired OCT data are different from each other between the first region and the second region. In this case, for example, when a subject is two-dimensionally scanned with measurement light through raster scanning, a step in a sub-scanning direction (also referred to as a "slow-axis direction") for defining an interval between scanning lines may be changed (refer to FIG. 4). A scanning speed in a main scanning direction (also referred to as a "fast-axis direction") between the first region and the second region may be changed (refer to FIGS. 5A to 5C). Alternatively, both of the methods may be used together.

Figure 4A:
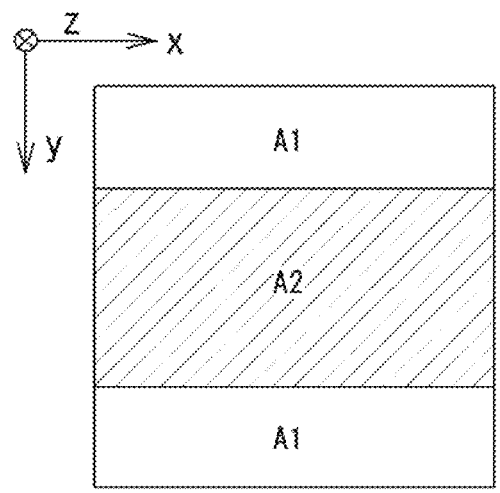
FIGS. 4A and 4B are diagrams for explaining a method of making a scanning density different in each region by changing a step in a sub-scanning direction.
Figure 4B:
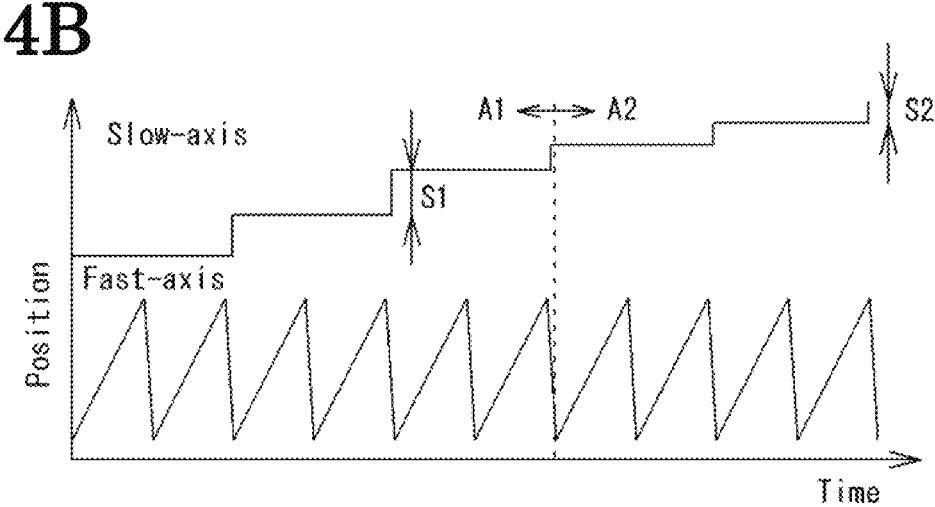

With reference to FIGS. 4A and 4B, a description will be made of an example of control of changing a step in the sub-scanning direction. Herein, a region of 3 mm×3 mm is imaged. In an imaging range, a region of ½ around the center in the sub-scanning direction is the second region (indicated by the reference sign A2), and a region of ¼ of each of upper and lower parts thereof is the first region (indicated by the reference sign A1). As illustrated in FIG. 4B, in each region, main scanning is performed twice per step in the sub-scanning direction. In FIG. 4A, a width of the second region corresponding to a half of the whole and in the sub-scanning direction is 1.5 mm. In a case where imaging is performed at 128 A-scans with respect to the width, a scanning density is 11.7 μm/A-scan. In other words, one step in the second region is 11.7 μm.

A width of the first region corresponding to ¼ of the whole and in the sub-scanning direction is 0.75 mm. In a case where imaging is performed at 42 A-scans with respect to the width, a scanning density is 17.9 μm/A-scan. In other words, one step in the first region is 17.9 μm.

In this case, the entire imaging range can be imaged for a required time of 82.8% compared with a case where the imaging range is imaged at 11.7 μm/A-scan (that is, fractional shortening FS=82.8%). To generalize, in a case where a proportion of the first region is indicated by R, the number of scanning points of the first region is indicated by NL, and the number of scanning points of the second region is indicated by NH, the fractional shortening FS may be expressed by the following Equation (1).

$$FS = \frac{N_H(1-R) + N_L R}{N_H} = 1 - \left(1 - \frac{N_L}{N_H}\right)R \qquad (1)$$

Figure 5A:
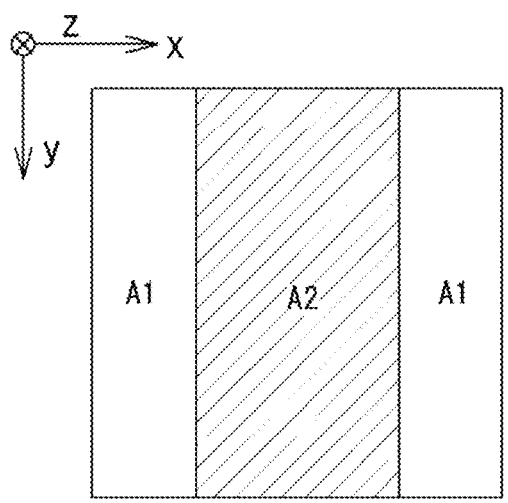
FIGS. 5A to 5C are diagrams for explaining a method of making a scanning density different in each region by changing a scanning speed for each region.
Figure 5B:
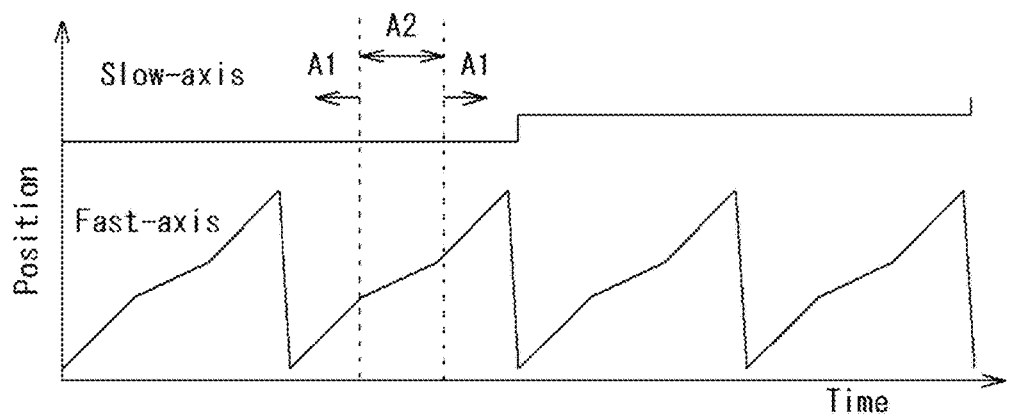
Figure 5C:
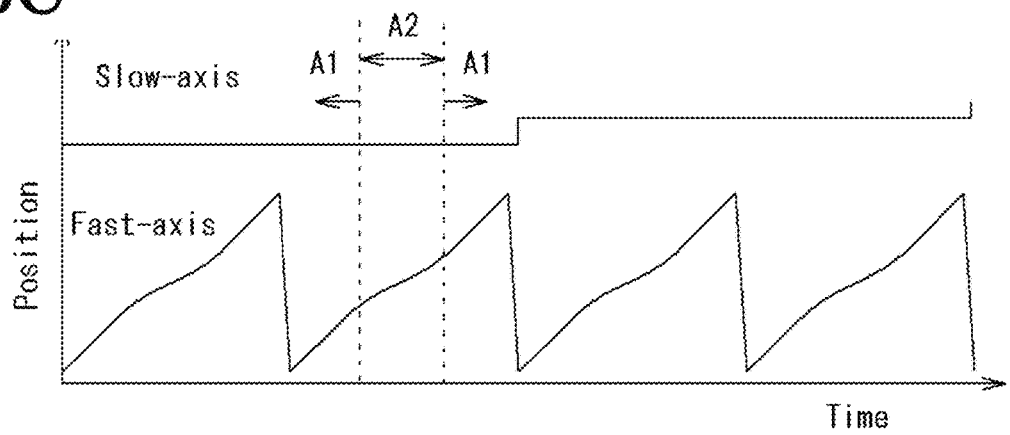

Next, with reference to FIGS. 5A to 5C, a description will be made of an example of control of changing a scanning speed in the main scanning direction. As illustrated in FIG. 5A, in a case where measurement light is applied to a scanning line crossing the first region and the second region, the control unit may change a scanning speed in each region in the middle of scanning of the scanning line. As illustrated in FIG. 5B, a scanning speed may be changed to a different value stepwise, and, as illustrated in FIG. 5C, a scanning speed may be continuously (smoothly) changed. FIG. 5C illustrates an example in which a scanning speed in the main scanning direction is changed in a tangential form.

<Overlap of Beam Spots at Scanning Points Adjacent to Each Other in Second Region>

As mentioned above, in a case where scanning amounts per unit time are different from each other between the first region and the second region, the control unit may control the scanning unit to cause beam spots of measurement light to overlap (partially overlap) each other between scanning points adjacent to each other in the second region. The scanning point mentioned here is a position where an OCT signal is acquired. The scanning points adjacent to each other are irradiated.

Figure 6A:
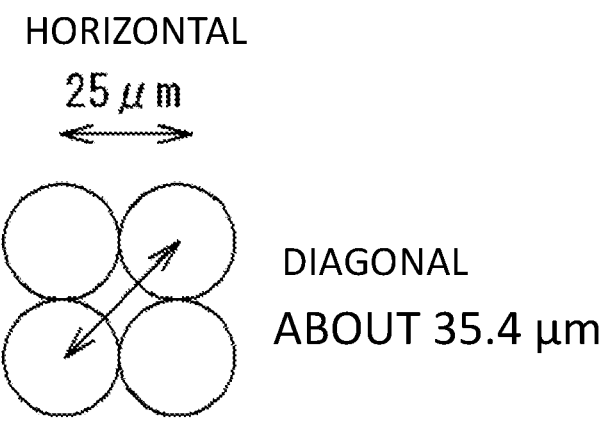
FIGS. 6A and 6B are diagrams for explaining a condition in which a gap is generated between scanning points and a condition in which a gap is not generated therebetween.
Figure 6B:
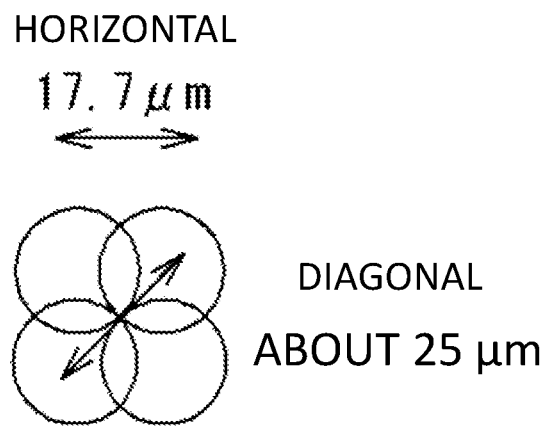

The control unit may cause at least two beam spots adjacent to each other in a scanning direction of the scanning unit to overlap each other. As a gap between scanning points becomes narrower, for example, a capillary can be detected without being omitted in MC data. More preferably, as illustrated in FIG. 6B, beam spots of two scanning points adjacent to each other in a diagonal direction for the scanning direction may overlap each other. A gap between beam spots is hardly generated in a region in which the beam spots overlap each other as mentioned above. As a result, for example, a capillary can be more favorably detected.

Here, with reference to FIGS. 6A and 6B, a description will be made of a preferable condition in a case where two beam spots adjacent to each other in the diagonal direction are made to overlap each other. In FIGS. 6A and 6B, a spot diameter is assumed to be about 25 μm. Here, as illustrated in FIG. 6A, assuming that a scanning interval (a distance between the centers of scanning points) in each of the X direction and the Y direction is about 25 μm which is the same as the spot diameter, it can be seen that a gap is generated at the center among four beam spots. For example, in an ophthalmic field, it is supposed that a target object used for imaging of motion contrast is smaller than the gap. For example, a size of a red blood cell which is an example of the target object is about 8 and a minimum size of a capillary is about 2 μm. Therefore, in a case where there is a gap described above, there may be a case where a target object is not irradiated, and thus motion contrast cannot be suitably drawn.

In contrast, as illustrated in FIG. 6B, in a case where a relationship of "a scanning interval in the diagonal direction<a spot diameter of a beam spot" is established, beam spots of two scanning points adjacent to each other in the diagonal direction for the scanning direction can be made to overlap each other, and thus a gap is not generated. In the above-described way, a capillary can be detected without being omitted.

In the present embodiment, the first region and the second region may be determined by taking into consideration a spot diameter of a beam spot at each scanning point on a subject. For example, in a case where a fundus of a subject eye is imaged as a subject, in the OCT apparatus of the present embodiment, measurement light turns centering on the anterior ocular segment, but a spot diameter of a beam spot may differ at each position of the fundus due to the fundus being curved. In this case, in a case where a beam waist position is set with the fundus center as a reference, a spot diameter of a beam spot is larger in the fundus periphery than in the fundus center. Therefore, in this case, the fundus center is set as the second region, the fundus periphery which is a peripheral portion thereof is set as the first region, and an interval between scanning points in the fundus center is relatively small. Consequently, a blood vessel is easily detected without being omitted in the entire range of the fundus.

<Remapping Process of OCT Data>

In a case where scanning is performed along a scanning line crossing the first region and the second region, and a scanning speed is changed depending on a region, a remapping process may be performed such that a difference in intervals of scanning points between the first region and the second region may be corrected. Since the number of scanning points per scanning amount in the first region is smaller than in the second region, in a case where scanning points are simply disposed, an expanded or contracted image is obtained. Therefore, in the remapping process, OCT data for an intermediate point between consecutive scanning points in the first region may be interpolated on the basis of neighboring OCT data. Various methods may be used as an interpolation method. For example, any one of a "nearest neighbor method", a "bilinear method", a "bicubic method", and a "Lanczos method" may be used. For example, in a case where a scanning speed in the second region is a half of a scanning speed in the first region, a remapping process of making the number of pieces of OCT data in the first region twice may be performed. A boundary vicinity between the first region and the second region is more favorably drawn in MC data generated on the basis of OCT data after the remapping process.

<Number of Times of Repeatedly Acquiring OCT Signals which are Bases of MC Data Differs in Each Region>

As another example of an imaging sequence in which the number of A-scans per unit area in the second region is larger than in the first region, the number of times of repeatedly acquiring OCT signals used to obtain MC data may be set to be larger in the second region than in the first region. The number of times of repeatedly acquiring OCT signals used to obtain MC data may be, for example, the number of B-scans on an identical scanning line. However, there is no limitation thereto.

Figure 7A:
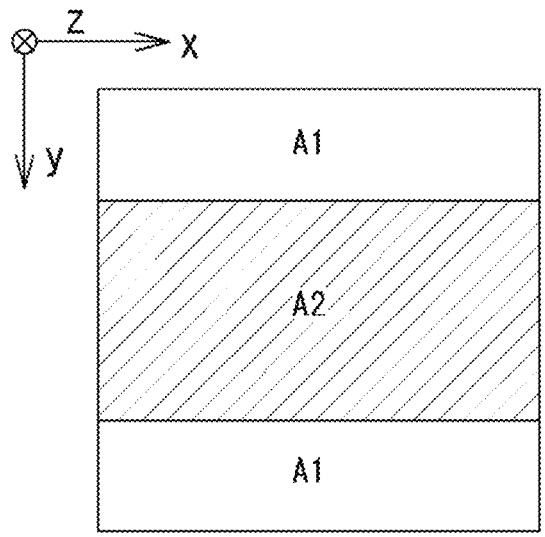
FIGS. 7A and 7B are diagrams for explaining a method of making a scanning density different in each region by changing the number of times of repeatedly acquiring an OCT signal for each region.
Figure 7B:
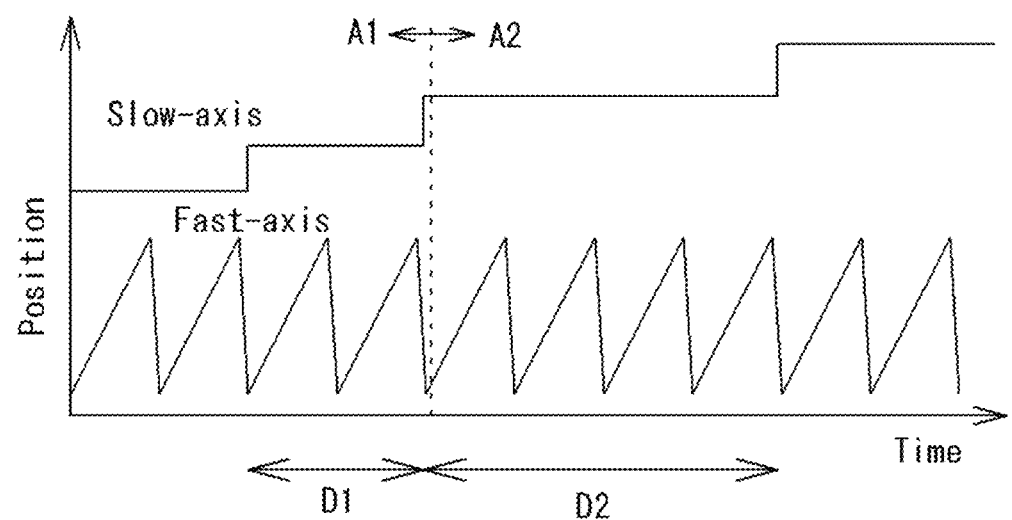

As an example, FIG. 7B illustrates a case where an OCT signal is repeatedly acquired twice at each scanning point in the first region (indicated by the reference sign A1), and the OCT signal is repeatedly acquired four times at each scanning point in the second region (indicated by the reference sign A2). As illustrated in FIG. 7B, in the first region, main scanning with measurement light is repeatedly performed twice per step (per range indicated by D1). In the second region, main scanning with measurement light is repeatedly performed four times per step (per range indicated by D2).

In a case where motion contrast calculation is performed at the shorted time interval, a single piece of MC data is obtained from an imaging result of the first region, and three pieces of MC data are obtained from an imaging result of the second region, on the basis of the OCT signals obtained through the operation. The three pieces of MC data obtained in the second region are added and averaged, and thus an S/N ratio of the second region is improved. Here, as illustrated in FIG. 7B, in a case where imaging is performed four times in a half region (hatched portion) of the entire imaging range as the second region, and imaging is performed twice in the rest half region as the first region, fractional shortening of an imaging time is 75% compared with a case where imaging is performed four times in the whole region. To generalize, in a case where a proportion of the first region is indicated by R, the number of times of imaging (the number of times of repeatedly acquiring OCT signals) in the first region is indicated by NL, and the number of times of imaging in the second region is indicated by NH, the fractional shortening FS may be expressed by the following Equation (2).

$$FS = \frac{N_H(1-R) + N_L R}{N_H} = 1 - \left(1 - \frac{N_L}{N_H}\right)R \quad (2)$$

As another method of improving an S/N ratio of MC data for the second region more than for the first region, there is a method in which an acquisition time (an exposure time at a scanning point) for an OCT signal at each position in the second region is longer than in the first region.

A time interval between OCT signals at each scanning point may be shorter in the second region than in the first region. In this case, the time required to acquire a plurality of OCT signals which are bases of MC data and per unit area may tend to be shorter in the second region than in the first region.

Figure 8:
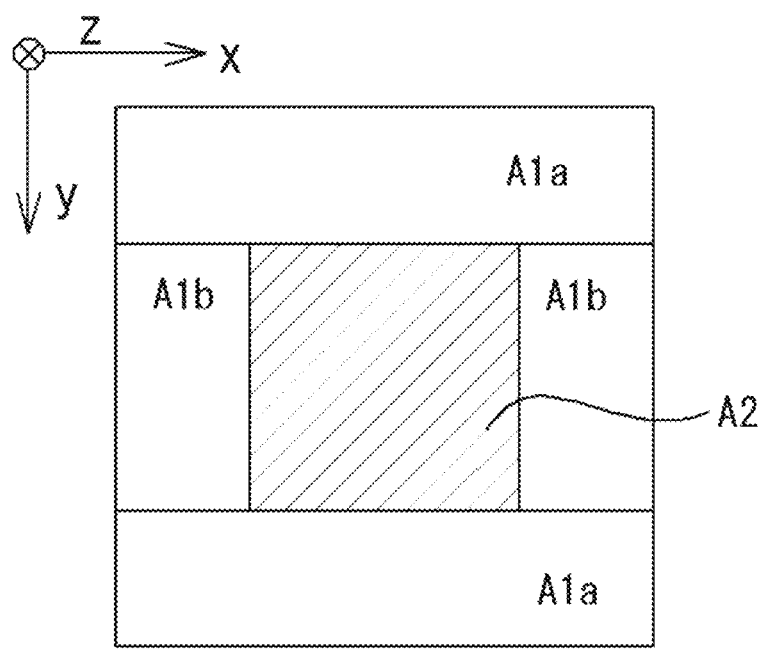
FIG. 8 is a diagram for explaining an imaging method of making a scanning density and the number of times of repeatedly acquiring an OCT signal different in each region.

Two or more of a scan density, the number of times of repeated acquisition, an exposure time, and a time interval may be made to differ in each region of an imaging range. For example, as in an example illustrated in FIG. 8, a region may be divided into a plurality of regions, and imaging may be performed. As an example, central regions indicated by the reference signs A2 and A1b in the Y direction are regions in which the number of times of repeated acquisition is four. Among the regions, an OCT signal is acquired in a relatively high scanning density in the central region indicated by the reference sign A2, and an OCT signal is acquired in a relatively low scanning density in the regions indicated by the reference sign A1b. In the regions indicated by the rest reference sign A1, the number of times of repeated acquisition is two and is small, and an OCT signal is acquired in a relatively low scanning density.

<Setting of Imaging Condition for MC Data>

The OCT apparatus may be further provided with a setting unit which sets an imaging condition for MC data on a subject.

The setting unit may set at least one of, for example, an imaging range of MC data, whether or not OCT data acquisition densities in each region of the imaging range are different from each other, and positions, sizes, and shapes of the first region and the second region. The control unit may also function as the setting unit, and a separate processor may function as the setting unit. The setting unit may set an imaging condition for MC data on the basis of, for example, image data acquired in advance.

<Setting of Imaging Range>

The setting unit may set an imaging range as one of imaging conditions. The imaging range may be one-dimensional, and may be two-dimensional, with respect to the XY directions (directions orthogonal to the depth (Z) direction). In a case of the one-dimensional imaging range, for example, MC data may be acquired through line scanning with respect to a single scanning line, and, in a case where of the two-dimensional imaging range, the imaging range may have a spherical shape, and, for example, MC data may be acquired through raster scanning. An imaging range may be radial, and, for example, MC data may be acquired through radial scanning.

<Setting of OCT Data Acquisition Density and Number of Times of Repeated Acquisition for Imaging Range>

The setting unit may set whether or not OCT data acquisition densities are different from each other in an imaging range as one of imaging conditions. For example, the setting unit may select an imaging mode from a variable density mode and a fixed density mode. The variable density mode is an imaging mode in which MC data is imaged in a partially high density. Specifically, the variable density mode is a mode in which the first region and the second region are set in an imaging range, and imaging is performed.

The fixed density mode is an imaging mode in which MC data is imaged in a fixed density (predefined density) in each region. In the fixed density mode, for example, the entire imaging range may be imaged in the same density as that in the first region or the second region in the variable density mode, and the entire imaging range may be imaged in a density which is different from that in either one thereof. Any density may be settable.

<Alert>

In the fixed density mode, or in the first region in the variable density mode, in a case where a scanning density is less than a predetermined threshold value, an alert may be output. As the alert, for example, attention sentences may be displayed. For example, the alert may be output when the following Equation (3) is established.

$$\sqrt{\left(\frac{F_x}{N_x}\right)^2 + \left(\frac{F_y}{N_y}\right)^2} > \alpha d \quad (3)$$

Here, in Equation (3), d is a spot diameter of a beam spot, Fx and Fy are respectively FOVs in an x direction and a y direction, and Nx and Ny are respectively the number of points in the x direction and the y direction. According to Equation (3), when an interval between scanning points in the diagonal direction exceeds α times the spot diameter, the alert is output. α may be a numerical value of 1 or more, and may be changeable as appropriate.

<First Region and Second Region are Selected from Among Patterns Prepared in Advance>

The first region and the second region in an imaging range may be set by the setting unit along with the imaging range. For example, positions of the first region and the second region may be defined in advance in an imaging range. One or more of disposition patterns of the first region and the second region in an imaging range may be prepared, and a disposition pattern may be automatically or manually selected such that the first region and the second region are set.

For example, in a case where the present embodiment is applied to an ophthalmic field, the setting unit may set a disposition pattern in which the second region is set around the macular fovea centralis, and the first region is set outside thereof. For example, the second region may be a region of 3 mm×3 mm around the macular fovea centralis. The first region is set to a region of 9 mm×9 mm outside the region of 3 mm×3 mm. However, a size of each region is not limited thereto. In diagnosis of age-related macular degeneration, the occurrence of choroidal neovascularization (CNV) is checked, and detailed MC data is necessary for the macular fovea centralis. In the disposition pattern, the second region has the size of 3 mm×3 mm, a range required to diagnosis of CNV is included in the second region. The outer region thereof is used for diagnosis of, for example, branch retinal vein occlusion (BRVO) and diabetic retinopathy (DR). However, in this case, the presence or absence of a nonperfused area (NPA) is only checked, and information regarding a fine blood vessel is not necessarily required. In the disposition pattern, the outer region corresponds to the first region. Therefore, the above-described disposition pattern is set, and thus it is considered that MC data having a necessary information amount in each part can be acquired in a shorter imaging time.

In a case where a disposition pattern is manually selected from among a plurality of disposition patterns prepared in advance, the setting unit may include an instruction reception portion which receives an instruction signal for an examiner setting a disposition pattern. For example, there may be selection of any one of options including two or more of a "first pattern" in which the first region and the second region are disposed in vertical stripes, a "second pattern" in which the first region and the second region are disposed in horizontal stripes, and a "third pattern" in which the second region is set in a part of the entire imaging range in each of the XY directions. A plurality of patterns in which either one of a ratio between the first region and the second region and a positional relationship between the regions differs in any one of the respective patterns may be further prepared, and any one may be selected from there among.

<Imaging Range is Set Based on Image Data Acquired in Advance>

The setting unit may set an imaging range of MC data on the basis of image data acquired in advance. The image data acquired in advance may be an image captured as a still image, and may be a moving image. The image data acquired in advance may be, for example, image data acquired in advance by using the OCT optical system. Consequently, an imaging range can be set on the basis of the image data acquired by using the OCT optical system, and thus setting of the imaging range can be performed with high accuracy. In this case, the image data may be, for example, MC data, and may be an OCT signal (OCT data). The MC data may be, for example, B-scan MC data, may be front MC data, and may be three-dimensional MC data. The OCT signal may be B-scan OCT data, may be front OCT data, and may be three-dimensional OCT data.

The image data acquired in advance may be, for example, image data acquired in advance by using an optical system which is different from the OCT optical system. In this case, the optical system which is different from the OCT optical system may be, for example, a front imaging optical system which includes an optical detector which is different from that of the OCT optical system, and captures a front image of a subject. For example, in a case where a subject is the fundus, the front imaging optical system may be a fundus camera optical system, and may be a scanning laser ophthalmoscope (SLO) optical system. The front imaging optical system may be a laser speckle flowgraphy (LSFG) for measuring a blood flow of the fundus. The setting unit may set an imaging range of MC data on the basis of examination data acquired in advance by using an ophthalmic examination apparatus without being limited to the image data. The examination data may be, for example, a visual field measurement result (which is useful to obtain MC data of the fundus) acquired in advance by using a perimeter. The examination data may be, for example, examination data (which is useful to obtain MC data of the anterior ocular segment) acquired in advance by using a corneal shape measurement apparatus, and an imaging range of MC data may be set on the basis of the examination data.

An apparatus configuration for obtaining the image data in advance may be provided in the OCT apparatus according to the present embodiment, and may be disposed in a casing separate from the OCT apparatus according to the present embodiment. In a case where image data is acquired in the separate case, the image data may be sent to the OCT apparatus via wired or wireless communication means.

The setting unit may analyze image data acquired in advance, and may set an imaging range of MC data on the basis of an analysis result. Consequently, it is possible to easily set an imaging range of MC data. The image data may be analyzed, for example, through image processing.

In a case where image data is analyzed, the setting unit may specify a part of interest by analyzing image data acquired in advance, and may set an imaging range to include the specified part of interest. The part of interest may be, for example, an abnormal part of a subject, and may be a feature part of the subject. Regarding a method of specifying a part of interest, for example, a part of interest may be specified through image processing by using an image processing program which is created to specify a part of interest by using image features (for example, a shape, luminance, and a size) of the part of interest.

In a case where the part of interest is specified, for example, the setting unit may automatically set an imaging range such that the part of interest is included in the imaging range. In this case, for example, the setting unit may change a size of the imaging range according to a size of the specified part of interest. Also in this case, the part of interest may be set as the second region, and the rest imaging range may be set as the first region. In a case where there are a plurality of parts of interest, or a part of interest is widely present, the setting unit may set, for example, a plurality of imaging ranges. In this case, each region of interest may be set as the second region, and the rest region may be set as the first region.

In a case where an imaging range is set in relation to a part of interest, the setting unit may analyze, for example, image data acquired in advance so as to specify a part of interest of a subject, and may display a position of the specified part of interest on the display unit. For example, the setting unit may be able to set an imaging range on the basis of the position of the part of interest on the display unit.

In a case where an imaging range of MC data is set on the basis of an analysis result, the above-described method is only an example, and the setting unit may set the imaging range of MC data on the basis of, for example, an analysis parameter (for example, an analysis value) obtained when image data is analyzed. In this case, the image data acquired in advance may be MC data. For example, the setting unit may obtain a blood vessel density of at least a part of a subject by analyzing the MC data acquired in advance, and may set the first region and the second region with a region in which the blood vessel density exceeds a threshold value as a part of interest. Of course, a region in which the blood vessel density is less than a threshold value may be a part of interest. For example, an arcade blood vessel may be detected, an inner region thereof may be set as the second region, and an outer region thereof may be set as the first region. Conversely, the inner region may be set as the first region, and the outer region may be set as the second region. In a case where an analysis parameter is obtained, the setting unit may divide image data into a plurality of regions in the XY directions, and may obtain an analysis parameter for each separate region.

In a case where an imaging range of MC data is set on the basis of an analysis result, a normal eye database regarding a blood vessel of a subject may be used for a determination process of whether or not a region is normal. The setting unit may set an imaging range on the basis of a result of the determination process, may set, for example, a region determined as being abnormal as an imaging range, and may set a region determined as being normal as an imaging range.

For example, the setting unit may perform a process of determining whether or not a region is normal by using a normal eye database regarding a blood vessel density in relation to a blood vessel density of a subject obtained through analysis of MC data acquired in advance, and may set an imaging range on the basis of a determination result.

The setting unit may obtain a difference extent between MC data acquired in advance and a normal eye database (for example, a blood vessel model of a normal eye) regarding a blood vessel shape through image processing, may perform a process of determining whether or not a region is normal on the basis of the difference extent, and may set an imaging range on the basis of a determination result.

In a case where an analysis parameter (for example, a blood vessel density or a blood vessel shape) of a fundus blood vessel is obtained on the basis of MC data, the analysis parameter may be corrected according to an ocular axial length value of a subject eye. Consequently, it is possible to correct a data acquisition region difference caused by an ocular axial length difference. As described above, in a case where a fundus analysis parameter is compared with the normal eye database, accurate comparison can be performed.

In setting of an imaging range based on an analysis parameter, the image data acquired in advance may be OCT data. For example, the setting unit may obtain a thickness of at least a part of a subject by analyzing the OCT data acquired in advance, and may set a region in which the thickness exceeds a threshold value as an imaging range. Of course, a region in which the thickness is less than a threshold value may be set as an imaging range. In this case, the first region and the second region may be separated from each other depending on a thickness difference. As another example of setting an imaging range, the setting unit may include an instruction reception portion which receives an instruction signal for an examiner setting an imaging range of MC data. The setting unit may set an imaging range of MC data on the basis of an input signal from the instruction reception portion. Consequently, for example, a part desired by the examiner may be set as an imaging range. In this case, for example, image data acquired in advance may be displayed on the display unit, and the setting unit may set an imaging range of MC data on the image data acquired in advance on the basis of an instruction signal from an operation unit. The setting unit may perform electronic display corresponding to an imaging range on MC data. At least one of a size and a position of the imaging range may be changeable. The electronic display may be changed depending on a size or a position of the imaging range.

Here, front MC data or front OCT data obtained by the OCT optical system is used as the image data acquired in advance, and, thus, for example, the OCT data in a direction orthogonal to a depth direction is two-dimensionally provided, so that an imaging range can be accurately set.

The setting unit may be able to set, for example, a partial three-dimensional region of a subject as an imaging range. Consequently, MC data regarding the partial three-dimensional region of the subject can be acquired.

An imaging range of MC data set by the setting unit may be narrower than an imaging range of image data acquired in advance. Consequently, for example, MC data regarding a part of interest of image data can be acquired. In this case, regarding an imaging range, an imaging range in at least a direction orthogonal to a depth direction may be narrow.

<Application to Subject Eye>

The OCT apparatus of the present embodiment is applicable to, for example, an ophthalmic OCT apparatus which acquires an OCT signal of an eye (for example, the anterior ocular segment or the fundus). In this case, the image data acquired in advance may be, for example, front MC data of an eye or front OCT data of an eye. The front MC data of an eye (or the front OCT data of an eye) may be generated on the basis of, for example, three-dimensional MC data of an eye (or the three-dimensional OCT data of an eye), and may be acquired by generating three-dimensional data as an image with respect to at least a partial region in a depth direction.

The front MC data of an eye (or the front OCT data of an eye) may be acquired by calculating three-dimensional MC data (or three-dimensional OCT data) with respect to all layer regions in the depth direction.

The front MC data of an eye (or the front OCT data of an eye) may be acquired by calculating three-dimensional MC data (or three-dimensional OCT data) with respect to some specific layer regions in the depth direction. A calculation method may be an integration process, and may be other methods (for example, histogram calculation). For example, data regarding the specific layer regions may be segmented for each layer through a segmentation process on three-dimensional MC data (or three-dimensional OCT data).

For example, an imaging range in which a state of a specific layer is taken into consideration can be set by setting an imaging range of MC data by using front MC data (or front OCT data) regarding a specific layer region of the fundus. Since two-dimensional information is provided in a direction orthogonal to the depth direction, for example, setting of an imaging range regarding a part of interest can be performed with high accuracy.

A subject may be an eye (the anterior ocular segment or the fundus), an outer part of a living body such as a skin, or a material other than a living body.

Example

Hereinafter, with reference to the drawings, a description will be made of an OCT apparatus of the present example according to the present embodiment. An OCT apparatus 1 illustrated in FIG. 1 processes an OCT signal acquired by an OCT device 10.

The OCT apparatus 1 includes, for example, a control unit 70. The control unit 70 is realized by, for example, a general central processing unit (CPU) 71, a ROM 72, and a RAM 73. The ROM 72 stores, for example, an OCT signal processing program for processing an OCT signal, various programs for controlling an operation of the OCT device 10, and initial values. For example, the RAM 73 temporarily stores various pieces of information. The CPU 71 may be configured with a plurality of control units (that is, a plurality of processors).

As illustrated in FIG. 1, the control unit 70 is electrically connected to, for example, a storage unit (for example, a nonvolatile memory) 74, an operation unit 76, and a display unit 75. The storage unit 74 is, for example, a non-transitory storage medium which can hold stored contents even though the supply of power is stopped. For example, a hard disk drive, a flash ROM, or a detachable USB memory may be used as the storage unit 74.

The operation unit 76 receives various operation instructions from an examiner. The operation unit 76 outputs a signal corresponding to an input operation instruction to the CPU 71. As the operation unit 76, for example, at least one user interface of a mouse, a joystick, a keyboard, and a touch panel may be used.

The display unit 75 may be a display mounted on a main body of the apparatus 1, and may be a display connected to the main body. For example, a display of a personal computer (hereinafter, also referred to as a "PC") may be used. A plurality of displays may be used together. The display unit 75 may be a touch panel. In a case where the display unit 75 is a touch panel, the display unit 75 may also be used as the operation unit 76. The display unit 75 displays, for example, an OCT image or a motion contrast image acquired by the OCT device 10.

The OCT apparatus 1 of the present example is connected to, for example, the OCT device 10. As a connection method, a wireless connection method may be used, a wired connection method may be used, and both of the methods may be used. The OCT apparatus 1 may be integrally configured to be stored in the same casing as that of the OCT device 10, and may be configured separately therefrom. The CPU 71 may acquire at least one piece of OCT data of an OCT signal, motion contrast data, and an Enface image, from the connected OCT device 10. Of course, the CPU 71 may not be connected to the OCT device 10. In this case, the CPU 71 may acquire OCT data captured by the OCT device 10 via a storage medium.

<OCT Device>

Figure 2:
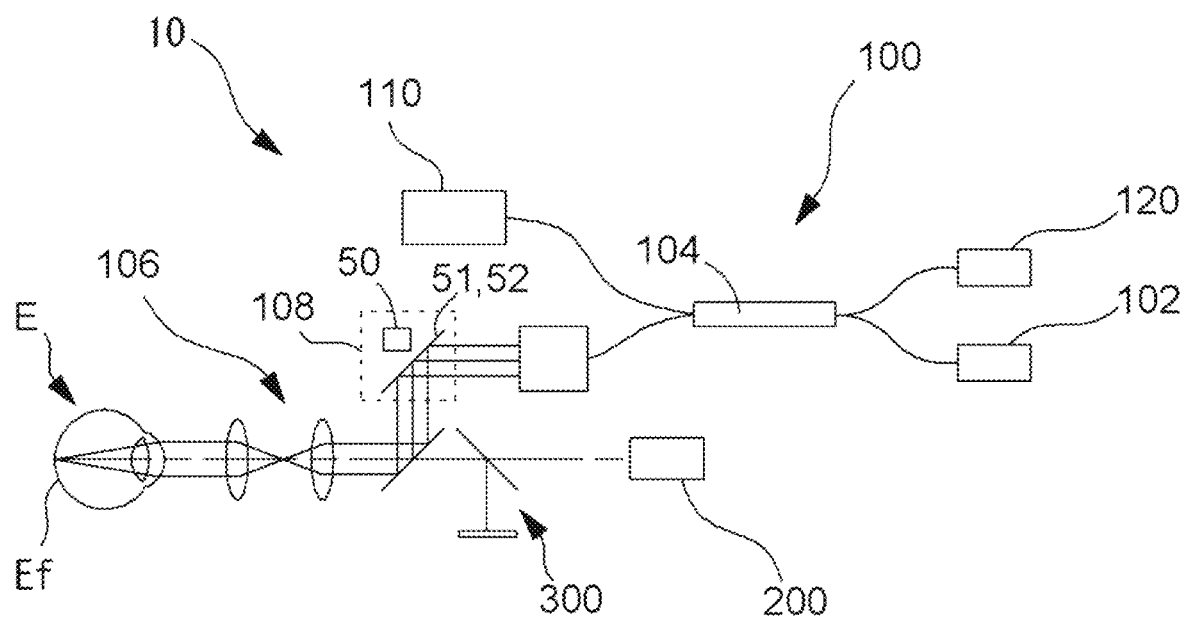
FIG. 2 is a diagram illustrating an example of an optical system of an OCT device in the Example.

Hereinafter, with reference to FIG. 2, the OCT device 10 will be described briefly. For example, the OCT device 10 irradiates a subject eye E with measurement light, and acquires an OCT signal acquired on the basis of reflected light thereof and the measurement light. The OCT device 10 mainly includes, for example, an OCT optical system 100.

<OCT Optical System>

The OCT optical system 100 irradiates the subject eye E with measurement light, and detects an interference signal between reflected light thereof and the reference light. The OCT optical system 100 mainly includes, for example, a measurement light source 102, a coupler (light splitter) 104, a measurement optical system 106, a reference optical system 110, and a detector 120.

The OCT optical system 100 is a so-called optical coherence tomography (OCT) optical system. In the OCT optical system 100, the coupler 104 splits light emitted from the measurement light source 102 into measurement light (sample light) and reference light. The split measurement light is guided to the measurement optical system 106, and the reference light is guided to the reference optical system 110. The measurement light is guided to the fundus Ef of the subject eye E via the measurement optical system 106. Thereafter, interference light as a result of measurement light reflected by the subject eye E and the reference light is received by the detector 120.

The measurement optical system 106 includes, for example, a scanning unit (for example, an optical scanner) 108. The scanning unit 108 changes a scanning position of measurement light on the subject eye so as to change an imaging position on the subject eye. For example, the CPU 71 controls an operation of the scanning unit 108 on the basis of set scanning position information, and acquires an OCT signal on the basis of a light reception signal detected by the detector 120.

For example, the scanning unit 108 scans the fundus with measurement light in the XY directions (transverse direction). The scanning unit 108 is disposed at a position substantially conjugate to the pupil. For example, the scanning unit 108 has two galvanomirrors 51 and 52, reflection angles thereof are adjusted to any angles by a drive mechanism 50. Consequently, a light beam emitted from the light source 102 changes its reflection (advancing) direction, and is applied in any direction on the fundus. In other words, a "B-scan" is performed on the fundus Ef. The scanning unit 108 may be configured to deflect light. For example, in addition to a reflection mirror (a galvanomirror, a polygonal mirror, or a resonant scanner), an acousto-optic modulator (AOM) which changes a light advancing (deflection) direction is used.

The measurement optical system 106 may include an objective optical system 109. The objective optical system 109 forms a turning point of measurement light in the anterior ocular segment of the subject eye. The turning point is formed at a position conjugate to the optical scanner 108 with respect to the objective optical system 109.

The reference optical system 110 generates reference light combined with reflected light acquired through reflection of the measurement light at the fundus Ef. The reference optical system 110 may be a Michelson type optical system, and may be a Mach-Zehnder type optical system. The reference optical system 110 is configured with, for example, a reflection optical system (for example, a reference mirror), returns light from the coupler 104 to the coupler 104 again by reflecting the light at the reflection optical system, and then guides the light to the detector 120. As another example, the reference optical system 110 is configured with a transmission optical system (for example, an optical fiber), transmits light from the coupler 104 therethrough so as to guide the light to the detector 120 instead of returning the light from the coupler 104.

The reference optical system 110 has, for example, a configuration in which an optical path length difference between measurement light and reference light is changed by moving an optical member on a reference optical path. For example, a reference mirror is moved in an optical axis direction. A configuration for changing an optical path length difference may be disposed in an optical path of the measurement optical system 106.

The detector 120 detects an interference state between measurement light and reference light. In a case of a Fourier domain OCT, a spectral intensity of interference light is detected by the detector 120, and a depth profile (A-scan signal) in a predetermined range is acquired through Fourier transform on the spectral intensity data.

As the OCT device 10, for example, a spectral-domain OCT (SD-OCT), a swept-source OCT (SS-OCT), or a time-domain OCT (TD-OCT) may be used.

In a case of the SD-OCT, a low coherence light source (broadband light source) is used as the light source 102, and the detector 120 is provided with a spectrometer which disperses interference light into respective frequency components (respective wavelength components). The spectrometer is configured with, for example, a diffraction grating and a line sensor.

In a case of the SS-OCT, a wavelength scanning type light source (wavelength variable light source) which changes an emitted wavelength temporally fast is used as the light source 102, and, for example, a single light receiving element is provided as the detector 120. The light source 102 is configured with, for example, a light source, a fiber ring resonator, and a wavelength selection filter. As the wavelength selection filter, there is, for example, a filter using a combination of a diffraction grating and a polygon mirror, or Fabry-Perot etalon.

<Front Imaging Optical System>

For example, a front imaging optical system 200 images the fundus Ef of the subject eye E from a front direction (for example, an optical axis direction of measurement light), and thus obtains a front image of the fundus Ef. The front imaging optical system 200 may include, for example, a second scanning unit which two-dimensionally scans the fundus with measurement light (for example, infrared light) emitted from a light source and a second light receiving element which receives reflected light from the fundus via a confocal opening disposed at a position substantially conjugate to the fundus, and may thus have an apparatus configuration of a so-called scanning laser ophthalmoscope (SLO) (for example, refer to JP-A-2015-66242). A configuration of the front imaging optical system 200 may be a so-called fundus camera type configuration (for example, refer to JP-A-2011-10944). The front imaging optical system 200 of the present example also uses some optical elements of the measurement optical system 106.

<Fixation Target Projection Unit>

A fixation target projection unit 300 has an optical system for guiding a visual line direction of the eye E. The projection unit 300 has a fixation target presented to the eye E, and may guide the eye E in a plurality of directions.

For example, the fixation target projection unit 300 has a visible light source which emits visible light, and two-dimensionally changes a presentation position of a target. Consequently, a visual line direction is changed, and thus an imaging part is changed. For example, in a case where a fixation target is presented from the same direction as an imaging optical axis, the central portion of the fundus is set as an imaging part. In a case where a fixation target is presented over the imaging optical axis, an upper part of the fundus is set as an imaging part. In other words, an imaging part is changed depending on a position of a fixation target with respect to the imaging optical axis.

The fixation target projection unit 300 may have various configurations such as a configuration in which a fixation position is adjusted depending on lighting positions of LEDs arranged in a matrix form, and a configuration in which light is applied from a light source by using an optical scanner, and a fixation position is adjusted by controlling lighting of the light source. The fixation target projection unit 300 may be of an internal fixation type, and may be of an external fixation type.

<Control Operation>

Figure 9:
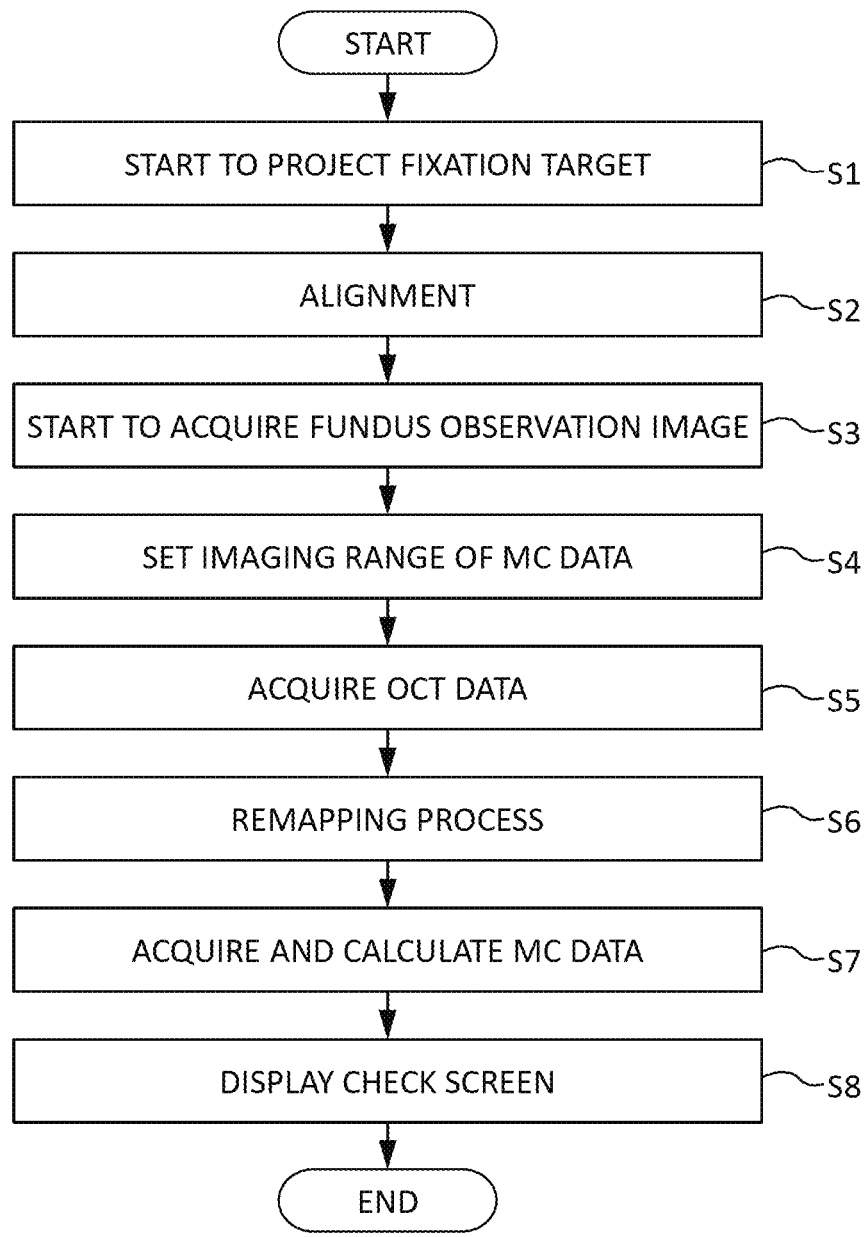
FIG. 9 is a flowchart illustrating a control operation of the present example.

In the OCT apparatus 1, with reference to a flowchart in FIG. 9, a description will be made of a control operation when OCT data acquired by the OCT device 10 is processed. The OCT apparatus 1 of the present example processes, for example, an OCT signal detected by the OCT device 10, so as to acquire motion contrast. In the following description, for example, the CPU 71 controls the OCT device 10 to acquire an OCT signal, but a control unit may be separately provided in the OCT device 10.

<Step S1 to Step S3>

First, for example, the CPU 71 controls the fixation target projection unit 300 to project a fixation target to an examinee (S1). The CPU 71 performs automatic alignment by controlling a drive unit (not illustrated) such that a measurement optical axis is located at the pupil center of the subject eye E on the basis of an anterior ocular segment observation image captured by an anterior ocular segment observation camera (not illustrated) (S2).

Thereafter, the CPU 71 controls the front imaging optical system 200 to start to acquire a front image of the fundus (S3). The front image may be displayed on the display unit 75. In the following description, the front image is used to set an imaging range of MC data. A live image based on the front image is used for application of measurement light to track movement of the eye, that is, the eyeball.

<Step S4: Setting of Imaging Range>

Next, the CPU 71 sets an imaging range of MC data on the basis of the front image. The imaging range may be automatically set on the basis of a feature portion detected from the front image, and may be manually set by an examiner. In a case where the examiner manually sets an imaging range of MC data, the front image may be displayed as a still image or a moving image on the display unit 75, and an imaging range may be set in a region designated by the examiner via the front image.

In the present example, an imaging range is set in the center of the fundus and the periphery thereof. In the present example, the first region and the second region are uniquely set according to an imaging range. In the following description, a near region of the fovea centralis is assumed to be the second region in the present example, and a peripheral region thereof is assumed to be the first region in the present example. The first region and the second region are consecutive regions, and the first region corresponds to a peripheral portion of the second region.

<Step S5: Acquisition of OCT Data>

Imaging of MC data in the imaging range is started by receiving a predetermined imaging trigger (step S5). The imaging trigger may be, for example, a release operation of the examiner on the operation unit 76 of the OCT apparatus 1. Completion of a predetermined process such as a process of setting an imaging range (step S4) may be used as an imaging trigger, so that imaging of MC data is automatically started.

The CPU 71 controls the OCT device 10 to image MC data in the set imaging range. For example, the CPU 71 scans the fundus Ef with measurement light. For example, as illustrated in FIG. 3A, the CPU 71 controls driving of the scanning unit 108, and thus applies the measurement light in the imaging range A1 on the fundus Ef. In FIG. 3A, the direction of the z axis is assumed to be an optical axis direction of measurement light. The direction of the x axis is perpendicular to the z axis, and is assumed to be a leftward-and-rightward direction of an examinee. The direction of the y axis is perpendicular to the z axis, and is assumed to be an upward-and-downward direction of the examinee.

For example, the CPU 71 applies measurement light in the x direction along scanning lines SL1, SL2, . . . , and SLn in the imaging range A including the first region A1 and the second region A2. Scanning with measurement light in a direction (for example, the x direction) intersecting the optical axis direction of the measurement light will be referred to as a "B-scan". An OCT signal obtained through a single B-scan is described here as an OCT signal of one frame. The CPU 71 acquires an OCT signal detected by the detector 120 while the measurement light is being applied. The CPU 71 stores, for example, the OCT signal acquired in the imaging range A, in the storage unit 74. As mentioned above, the imaging range A may be a scanner region in the x and y directions, in which a plurality of scanning lines in the x direction are arranged in the y direction. Therefore, the CPU 71 applies measurement light in a two-dimensional manner in the x and y directions, and obtains A-scan signal in the z direction at each scanning position. In other words, the CPU 71 acquires, for example, three-dimensional data.

In the present example, each of the scanning lines SL1, SL2, . . . , and SLn crosses both of the first region A1 and the second region A2. The CPU 71 controls the scanning unit 108 to change a scanning speed in the middle of scanning in each scanning line. Specifically, a scanning speed switches between scanning of the first region A1 and scanning of the second region A2. Here, for example, since a scanning range of the scanning unit 108 corresponding to each of the first region A1 and the second region A2 is known, a scanning speed may be changed depending on a displacement amount of the scanning unit 108. In the present example, driving of the scanning unit 108 is controlled such that a scanning speed in the first region A1 is lower than a scanning speed in the second region A2. As a specific example, a scanning speed in the second region A2 is a half of that in the first region A1. As a result, an interval between scanning points in the second region A2 is narrower than an interval (specifically, an interval between central positions) between scanning points in the first region A1. Specifically, an interval between scanning points in the second region A2 is a half of an interval between scanning points in the first region A1. In the above-described way, in the present example, OCT data which is a basis of MC data is acquired in the second region A2 in a density twice higher than in the first region A1.

In the present example, motion contrast is acquired on the basis of an OCT signal. The motion contrast may be, for example, information indicating a blood flow of a subject eye or a change in retinal tissue. In a case where the motion contrast is acquired, the CPU 71 acquires at least two OCT signals which are temporally different from each other with respect to an identical position in the subject eye. For example, the CPU 71 performs a plurality of B-scans at a time interval in each scanning line, and thus acquires a plurality of temporally different OCT signals. For example, the CPU 71 performs a first B-scan at a certain time, and performs a second B-scan in the same scanning line as in the first B-scan after a predetermined time elapses. The CPU 71 acquires an OCT signal detected by the detector 120 at this time so as to acquire a plurality of temporally different OCT signals.

Figure 3B:
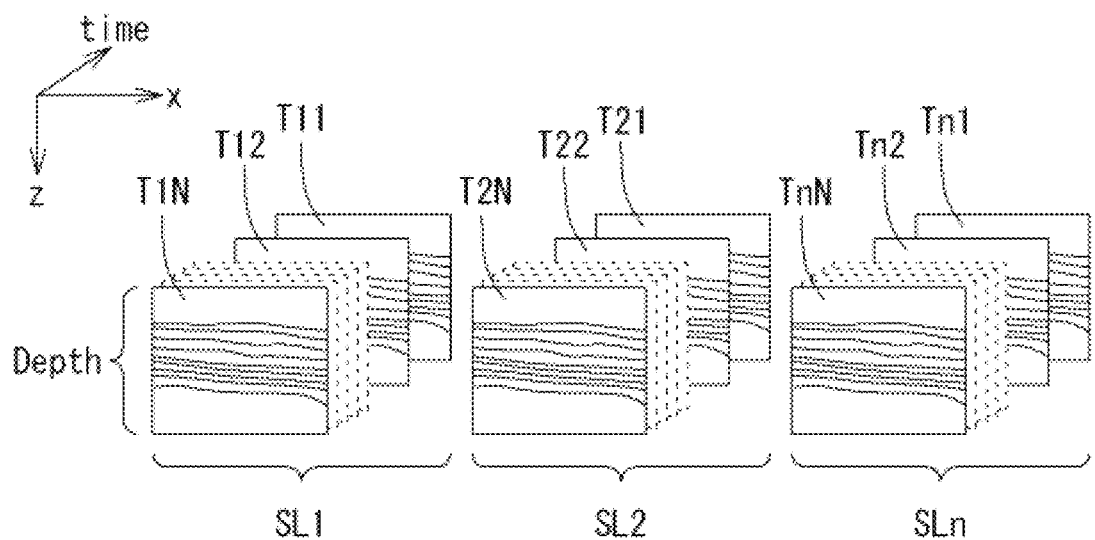
Figure 3C:
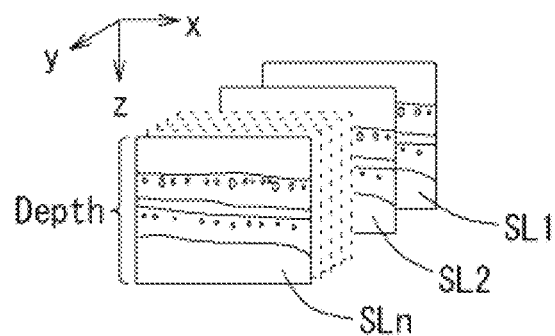

For example, FIG. 3B illustrates OCT signals acquired in a case where a plurality of temporally different B-scans are performed in the scanning lines SL1, SL2, . . . , and SLn. For example, FIG. 3B illustrates a case where the scanning line SL1 is scanned at times T11, T12, . . . , and T1N, scanning line SL2 is scanned at times T21, T22, . . . , and T2N, and scanning line SLn is scanned at times Tn1, Tn2, . . . , and TnN. As mentioned above, the CPU 71 may control the OCT device 10 to perform a plurality of temporally different B-scans in each scanning line, and may thus acquire a plurality of temporally different OCT signals. For example, the CPU 71 acquires a plurality of temporally different OCT signals at an identical position, and stores data thereof in the storage unit 74.

<Step S6: Remapping of OCT Data>

The OCT data acquired in the above-described way differs in terms of the number of scanning points per scanning amount in the first region A1 and the second region A2. When MC data is generated on the basis of a corresponding OCT signal during a period between the respective B-scans, a remapping process is preliminarily performed by the CPU 71. In the present example, OCT data obtained in a scanning range corresponding to the first region A1 is interpolated according to "nearest neighbor". In the present example, OCT data for an intermediate point between scanning points in the first region A1 is interpolated. In other words, in the present example, the number of scanning points in the first region A1 is increased and interpolated in inverse proportion to the scanning speed in the second region A2.

<Step S7: Acquisition of Motion Contrast>

In a case where the OCT signal is acquired as described above, the CPU 71 acquires motion contrast by processing the OCT signal. A method of calculating an OCT signal for acquiring motion contrast may include, for example, a method of calculating an intensity difference between complex OCT signals, a method of calculating a phase difference between complex OCT signals, a method of calculating an vector difference between complex OCT signals, a method of multiplying a phase difference and a vector difference of complex OCT signals by each other, and a method (correlation method) using a correlation between signals. In the present example, as an example, a description will be made of a method of calculating a phase difference as motion contrast.

For example, in a case where a phase difference is calculated, the CPU 71 performs Fourier transform on a plurality of OCT signals. For example, in a case where a signal at a position of an n-th frame (x,z) among N frames is indicated by An(x,z), the CPU 71 obtains a complex OCT signal An(x,z) through Fourier transform. The complex OCT signal An(x,z) includes a real number component and an imaginary number component.

The CPU 71 calculates a phase difference between at least two complex OCT signal A(x,z) which are acquired at different times at an identical position. For example, the CPU 71 calculates a phase difference by using the following Equation (4). For example, the CPU 71 may calculate a phase difference in each scanning line (refer to FIG. 3C), and may store data thereof in the storage unit 74. An in the equation indicates a signal acquired at a time TN, and * indicates a complex conjugate.

$$\Delta\Phi_n(x,z) = \arg(A_{n+1}(x,z) \times A_n^*(x,z)) \quad (4)$$

As described above, the CPU 71 acquires three-dimensional motion contrast data of the subject eye E on the basis of the OCT signals. As mentioned above, motion contrast is not limited to a phase difference, and an intensity difference or a vector difference may be acquired.

<Step S8: Display of Check Screen>

In a case where the subject eye is imaged, the CPU 71 displays, for example, an imaging result on the display unit 75. As the imaging result, at least motion contrast data (hereinafter, abbreviated to MC data) is displayed.

Figure 10:
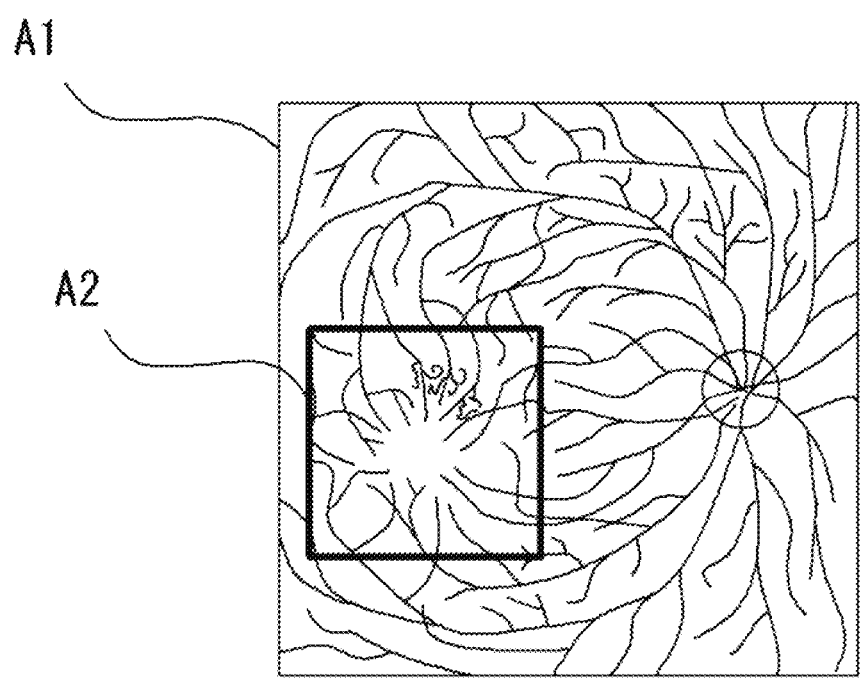
FIG. 10 illustrates an example of front MC data in the entire imaging range.

As an example, front MC data in the entire imaging range illustrated in FIG. 10 may be displayed. In the front MC data, the number of scanning points per scanning amount is set to be larger in the second region A2 corresponding to a central portion of the fundus than in the first region A1 corresponding to a peripheral portion thereof, and thus the front MC data is high-density MC data. With this display, for example, the examiner can favorably check a situation in which choroidal neovascularization (CNV) in the fundus central portion occurs and the presence or absence of a nonperfused area (NPA) in the entire imaging range from the front MC data on the screen.

Modification Examples

Hereinafter, modification examples of the present embodiment will be described.

<Panorama Imaging>

For example, MC data in the entire imaging range may be panorama data. The panorama data is generated, for example, by dividing the entire imaging range into a plurality of regions, and combining (collage) a plurality of pieces of MC data obtained in the respective regions with each other.

As a specific example, in a case where an imaging range is a region of 9 mm×9 mm, pieces of MC data are imaged nine times in an imaging range of 3 mm×3 mm, and are combined with each other, and thus panorama data corresponding to the imaging range is generated. In this case, high-density MC data may be imaged in the region of 3 mm×3 mm at the center as the second region, and low-density MC data in the other regions as the first region, and the pieces of data may be combined with each other. In this case, imaging of a plurality of pieces of MC data forming the panorama data may be continuously performed on the basis of a single release signal.

<Density Adjustment Based on Switching of Angle of View>

As an OCT device, a device which can switch an angle of view at which imaging can be performed has been recently proposed. For example, an angle of view can be switched by switching an objective optical system placed between the scanning unit and a subject eye. In the device of this type, a diameter of a beam spot on a subject may be changed along with an angle of view. For example, a scanning range of measurement light may be expanded by inserting a wide-angle attachment into the objective optical system 109 (in other words, an imaging range may be widened). The wide-angle attachment is inserted into the objective optical system 109, so as to increase a diameter of a beam spot on the fundus. However, in a case where a diameter of a beam spot is increased, a resolution is reduced.

In contrast, the measurement optical system may include, for example, a variable beam expander (light beam diameter adjustment unit) between the optical scanner 108 and the coupler 104. For example, in the present example, the control unit 70 may drive the variable beam expander according to insertion and detachment of the wide-angle attachment, and may thus reduce a diameter of a beam spot in an inserted state more than in a retreated state. Consequently, a reduction in a resolution due to insertion of the wide-angle at this time is suppressed. On the other hand, in a case where a diameter of a beam spot is reduced by driving variable beam expander, a gap of a beam spot is easily generated between scanning points adjacent to each other, and thus there may be disadvantageous in obtaining MC data.

Therefore, in obtaining MC data, the control unit 70 may change a scanning density (that is, the number of scanning points per angle of view) according to a diameter of a beam spot. For example, as described above, in a case where the wide-angle attachment is inserted such that an angle of view is increased, and a diameter of a beam spot is reduced by the light beam diameter adjustment unit, a plurality of temporally different OCT signals may be acquired in high scanning density in a retreated state of the wide-angle attachment, and MC data may be acquired on the basis of the OCT signals obtained in the above-described way. Favorable MC data can be obtained in both of before and after an angle of view is changed.

<Application to Apparatuses Other than OCT>

In the embodiment, the present disclosure has been described on the basis of the embodiment of the OCT apparatus. However, the present disclosure is not limited thereto, and the technique of the present disclosure may be applied to a scanning imaging apparatus (particularly, an ophthalmic imaging apparatus). For example, there is a scanning laser ophthalmoscope as the scanning imaging apparatus which is well known in an ophthalmic field, along with the OCT.

The scanning imaging apparatus includes at least a scanning optical system and a processor. The scanning optical system has a scanning unit. The scanning unit deflects light from a light source, and thus scans a subject with the light. The scanning optical system images the subject on the basis of return light from the subject.

A control unit executes an imaging sequence of consecutively imaging a first region on the subject and a second region adjacent to or partially overlapping with the first region on the basis of a predetermined trigger signal.

An operation described in < > in the embodiment may be performed in the imaging apparatus as appropriate. For example, <Overlap of beam spots at scanning points adjacent to each other in second region> may be applied. In this case, in an imaging sequence, the scanning unit may be controlled such that beam spots of light applied to two scanning points adjacent to each other in a scanning direction of the scanning unit overlap each other, in at least a part of scanning points in the second region. The control unit may control the scanning unit such that beam spots on two scanning points adjacent to each other in a diagonal direction with respect to the scanning direction of the scanning unit may overlap each other in at least a part of scanning points of OCT signals in the second region.

1 OCT apparatus
10 OCT device
70 control unit
71 CPU
72 ROM
73 RAM
74 storage unit
75 display unit
76 operation unit
100 OCT optical system
108 scanning unit
200 front imaging optical system

What is claimed is:

1. An OCT apparatus comprising:
an OCT optical system configured to acquire an OCT signal based on measurement light applied to a subject and reference light; and
a processor,
wherein the processor is configured to:
control the OCT optical system based on a predetermined trigger to execute an imaging sequence in which a plurality of temporally different OCT signals are acquired in each of a first region on a subject and a second region adjacent to or partially overlapping with the first region, and imaging conditions are different from each other between the first region and the second region, and
obtain OCT motion contrast data of the subject based on the plurality of OCT signals acquired through the imaging sequence in the first region and the second region; and
wherein the processor executes the image sequence in which times required to acquire the plurality of OCT signals per unit area are different from each other between the first region and the second region.

2. The OCT apparatus according to claim 1, wherein the processor executes the image sequence in which the number of A-scans per unit area is increased in the second region more than in the first region.

3. The OCT apparatus according to claim 2, wherein the processor executes the image sequence to acquire the OCT signals in higher density in the second region than in the first region.

4. The OCT apparatus according to claim 3, wherein the OCT optical system includes a scanning unit configured to deflect the measurement light and scan the subject with the measurement light, and
the processor controls the scanning unit to make scanning amounts per unit time different from each other between the first region and the second region so as to acquire different densities of the OCT signals between the first region and the second region.

5. The OCT apparatus according to claim 4, wherein the processor controls the scanning unit such that beam spots of the measurement light applied to two scanning points adjacent to each other in a scanning direction of the scanning unit overlap each other in at least a part of scanning points of OCT signals in the second region.

6. The OCT apparatus according to claim 5, wherein the processor further controls the scanning unit such that the beam spots on two scanning points adjacent to each other in a diagonal direction with respect to the scanning direction of the scanning unit overlap each other in at least a part of scanning points of OCT signals in the second region.

7. The OCT apparatus according to claim 3, wherein the processor is configured to perform a remapping process of correcting a difference in intervals of scanning points between the first region and the second region with respect to the plurality of OCT signals acquired through the imaging sequence, and afterward obtain the OCT motion contrast data based on the plurality of OCT signals after.

8. The OCT apparatus according to claim 2, wherein the processor controls the OCT optical system to increase the number of times of repeatedly acquiring the OCT signals in the second region more than in the first region.

9. The OCT apparatus according to claim 1, wherein the processor controls the OCT optical system to reduce a time interval between the OCT signals at each scanning point in the second region more than in the first region.

10. The OCT apparatus according to claim 1, wherein the processor controls the OCT optical system to lengthen an exposure time at each scanning point in the second region more than in the first region.

11. The OCT apparatus according to claim 1, wherein the processor sets either one or both of a position and a size of at least one of the first region and the second region.

12. The OCT apparatus according to claim 11,
wherein the OCT optical system is suitable to acquire an OCT signal of a fundus of a subject eye as the subject, and the processor sets the second region such that a macular part or a papilla part of the fundus of the subject eye is disposed at a center.

13. The OCT apparatus according to claim 11,
wherein the processor sets the second region at a position of interest based on position-of-interest information indicating the position of interest on a subject, and further sets the first region on a periphery of the second region.

14. The OCT apparatus according to claim 11,
wherein the processor sets the second region at a position on a subject designated by an examiner via an operation input unit, and further sets the first region on a periphery of the second region.

* * * * *